United States Patent
Gao et al.

(10) Patent No.: US 12,195,474 B2
(45) Date of Patent: Jan. 14, 2025

(54) PREPARATION METHOD OF ZALEPLON

(71) Applicants: Xinxiang Medical College, Xinxiang (CN); Anhui University of Technology, Maanshan (CN)

(72) Inventors: Qinghe Gao, Xinxiang (CN); Xinya Han, Maanshan (CN); Yongtao Xu, Xinxiang (CN); Yingchao Duan, Xinxiang (CN); Jieli Lv, Xinxiang (CN); Lizhen Fang, Xinxiang (CN); Yan Zhang, Maanshan (CN); Jufen Yan, Maanshan (CN); Yingying Li, Xinxiang (CN)

(73) Assignees: Xinxiang Medical College, Xinxiang (CN); Anhui University of Technology, Maanshan (CN)

( * ) Notice: Subject to any disclaimer, the term of this patent is extended or adjusted under 35 U.S.C. 154(b) by 588 days.

(21) Appl. No.: 17/568,851

(22) Filed: Jan. 5, 2022

(65) Prior Publication Data
US 2022/0259206 A1    Aug. 18, 2022

Related U.S. Application Data

(63) Continuation of application No. PCT/CN2021/102459, filed on Jun. 25, 2021.

(30) Foreign Application Priority Data

Feb. 18, 2021   (CN) .......................... 202110187247.9

(51) Int. Cl.
C07D 487/04    (2006.01)

(52) U.S. Cl.
CPC .................................. *C07D 487/04* (2013.01)

(58) Field of Classification Search
CPC ..................................................... C07D 487/04
See application file for complete search history.

(56) References Cited

U.S. PATENT DOCUMENTS

| | | | | |
|---|---|---|---|---|
| 4,626,538 A * | 12/1986 | Dusza | ................... | C07D 487/04 514/906 |
| 4,847,256 A * | 7/1989 | Tseng | ...................... | A61P 25/20 564/194 |
| 4,963,553 A * | 10/1990 | Tseng | ................... | C07D 487/04 514/233.2 |
| 5,126,340 A * | 6/1992 | Tseng | ................... | C07D 487/04 514/233.2 |
| 5,219,857 A * | 6/1993 | Tseng | ................... | C07D 487/04 514/233.2 |

\* cited by examiner

*Primary Examiner* — Timothy R Rozof

(57) ABSTRACT

A preparation method of zaleplon is provided and belongs to the technical field of pharmaceutical chemistry. The preparation method adopts simple and cheap m-nitrobenzaldehyde and triethylamine as raw materials, and constructs a core structure of zaleplon with high efficiency and high selectivity through a one-pot series reaction without transition metal catalysis, thereby avoiding the formation of isomers, reducing the generation of by-products, increasing the yield of target products and reducing the synthesis cost; and after simple nitro reduction modification, zaleplon is prepared. The method has the advantages of short preparation route, mild reaction conditions and simple operation, so the method is suitable for industrial production.

2 Claims, No Drawings

PREPARATION METHOD OF ZALEPLON

TECHNICAL FIELD

The invention belongs to the technical field of pharmaceutical chemistry, and particularly relates to a preparation method of zaleplon.

BACKGROUND

Zaleplon, whose chemical name is N-[3-(3-cyanopyrazolo[1,5-a]pyrimidine-7-yl)phenyl]-N-ethylacetamide, is a new kind of pyrazolopyrimidine sedative-hypnotic drug developed by Wyeth-Ayerst in the United States. In March 1999, the European Union approved zaleplon for insomnia, and in August 1999, the U.S. FDA (Food and Drug Administration) approved zaleplon for adult insomnia. Zaleplon was first sold in Denmark and Sweden in July 1999. Zaleplon, as a third-generation non-benzodiazepine sedative-hypnotic drug that has been applied in clinic, is a complete agonist of benzodiazepine ω1 receptor; zaleplon has the characteristics of short half-life, good curative effects, few side effects and no mental dependence. Zaleplon is mainly used for short-term treatment of adult insomnia. Zaleplon can help insomnia patients fall asleep quickly, shorten the time of falling asleep, prolong sleeping time and avoid frequent wakeups and reduce the number of awakenings. People live an increasingly busy life in 2020s. There will be a growing number insomniacs, and the demand for sedative-hypnotic drugs will also increase year by year. Therefore, zaleplon has a broad market prospect.

Zaleplon has the following chemical structural formula:

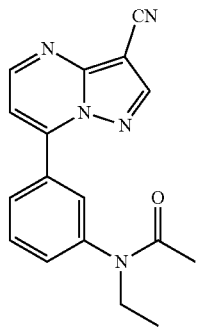 [SMILES: CCN(C(C)=O)c1cccc(-c2ccnc3c(C#N)cnn23)c1]

Among the published preparation methods of zaleplon, U.S. Pat. No. 4,626,538 in 1986 reported that N-(3-acetylphenyl) acetamide was used as raw material and condensed with N, N-dimethylformamide dimethyl acetal to obtain a condensate; then, under an argon atmosphere, the condensate was mixed with sodium hydride and stirred, cooled in ice bath, and added with iodine ethane dropwise for ethylation reaction; and finally, ethylated product is cyclized with equimolar 3-amino-4-cyanopyrazole in glacial acetic acid to obtain zaleplon. This synthetic route is short in steps, but complicated in operation, and the regioselectivity of cyclization reaction is poor (isomers are formed).

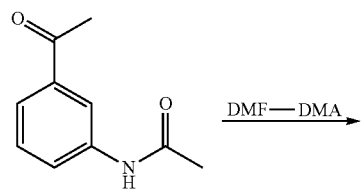

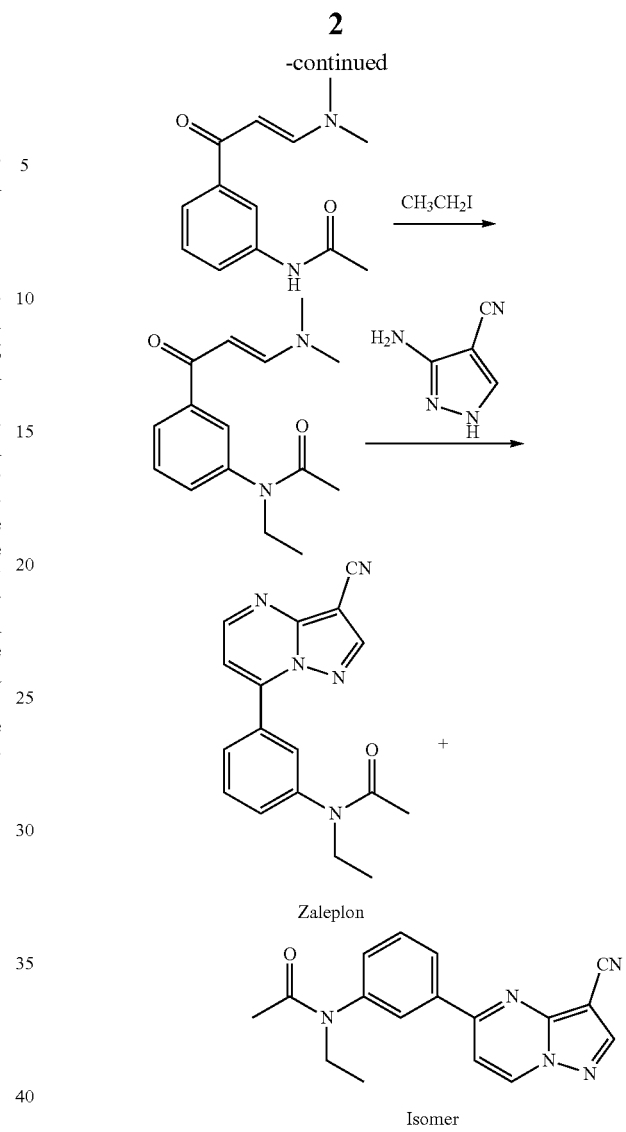

Zaleplon

Isomer

Although there have been continuous reports of perfection research, this synthetic route is still limited by cyclization reaction. For example, the preparation method reported by Huang Xuefeng, Li Yuyan, You Qidong, "Synthesis of Zaleplon", China Pharmacist, 2002, pp. 265-266, Vol. 5, No. 5 only pushed the starting material forward to acetophenone, which was converted into N-(3-acetylphenyl) acetamide after nitration, reduction and acetylation. Although the raw material is simpler, the extended synthetic route leads to lower overall yield, and the problem of regioselectivity in the cyclization reaction is still not solved, which is unfavourable for large-scale production.

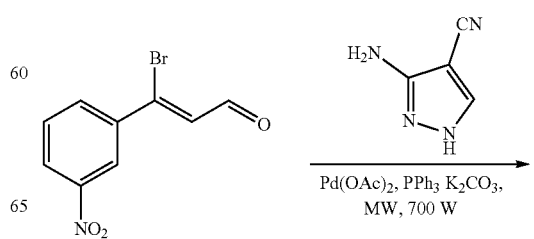

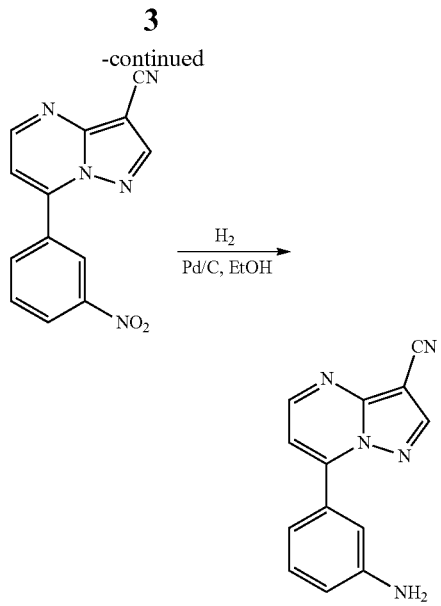

Kommuri Shekarrao et al., "Microwave-assisted palladium mediated efficient synthesis of pyrazolo[3,4-b]pyridines, pyrazolo-[3,4-b]quinolines, pyrazolo[1,5-a]pyrimidines and pyrazolo[1,5-a]quinazolines†", Royal Society of Chemistry, 2014, pp. 24001-24006 reported that the pyrazolopyrimidine fused ring was constructed first by coupling reaction with 3-bromo-3-(3-nitrophenyl) acrolein and 3-amino-4-cyanopyrazole as raw materials, palladium acetate as catalyst, triphenylphosphine as ligand and potassium carbonate as base under microwave conditions to avoid the generation of isomers. However, the expensive palladium catalyst was used, which led to complex subsequent treatment procedure and high costs for the reaction solution, and the raw material 3-bromo-3-(3-nitrophenyl) acrolein needed to be prepared in advance.

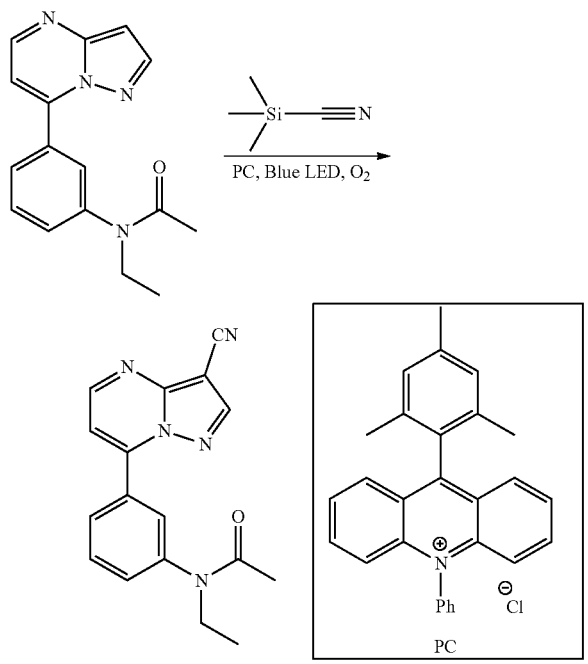

In 2020, Chinese patent CN107973800 reported that N-ethyl-N-(3 (pyrazolo[1,5-a]pyrimidine-7-yl)phenyl) acetamide was reacted with trimethylsilylaceonitrile under light in the reaction solvent containing acridine salt catalyst to prepare zaleplon directly. Although the preparation route was short and the yield was high, the raw material N-ethyl-N-(3-(pyrazolo[1,5-a]pyrimidine-7-yl)phenyl) acetamide needed multi-step pre-preparation.

SUMMARY

An objective of the invention is to overcome the shortcomings of the prior art, and provide a preparation method of zaleplon with short route, simple and cheap raw materials, simple operation, no transition metal catalysis and suitable for industrial production.

The invention adopts the following technical solution to achieve the above objective: a preparation method of zaleplon, which may include the following specific steps:

S1, preparing 7-(3-nitrophenyl) pyrazol[1,5-a]pyrimidine-3-nitrile having the following chemical structural formula 3, by using m-nitrobenzaldehyde having the following chemical structural formula 1, 3-amino-4-cyanopyrazole having the following chemical structural formula 2 and triethylamine as raw materials in presences of an iodine reagent, an oxidant and a solvent, and a synthetic route therefor being as follows:

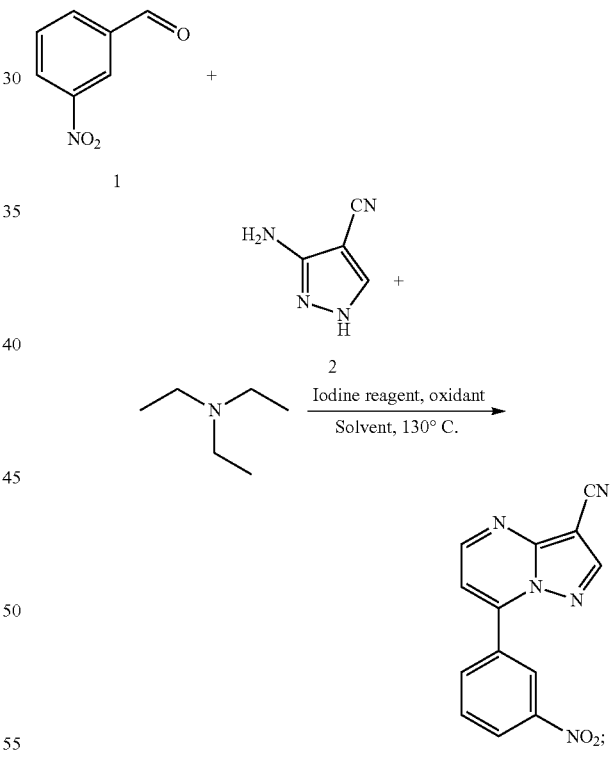

where the iodine reagent is one selected from a group consisting of ammonium iodide, N-iodosuccinimide, elemental iodine and tetrabutylammonium iodide; the oxidant is one selected from a group consisting of di-tert-butyl peroxide and dicumyl peroxide; and the solvent is one selected from a group consisting of toluene, chlorobenzene, 1,4-dioxane, acetonitrile and tetrahydrofuran.

S2, subjecting the 7-(3-nitrophenyl) pyrazol[1,5-a]pyrimidine-3-nitrile to one-pot reductive acetylation with iron powder and glacial acetic acid to obtain a compound having the following chemical structural formula 4, and a synthetic route therefor being as follows:

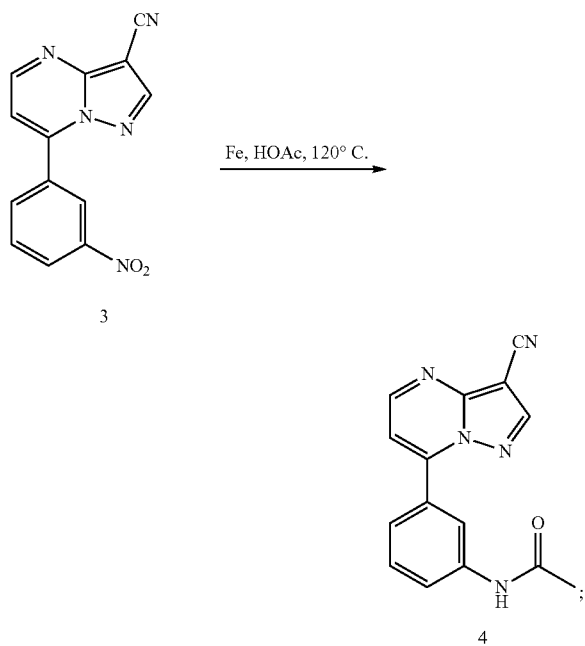

and

S3, ethylating the compound having the chemical structural formula 4 with bromoethane to obtain a compound having the following chemical structural formula 5, that is, the zaleplon as target product, and a synthetic route therefor being as follows:

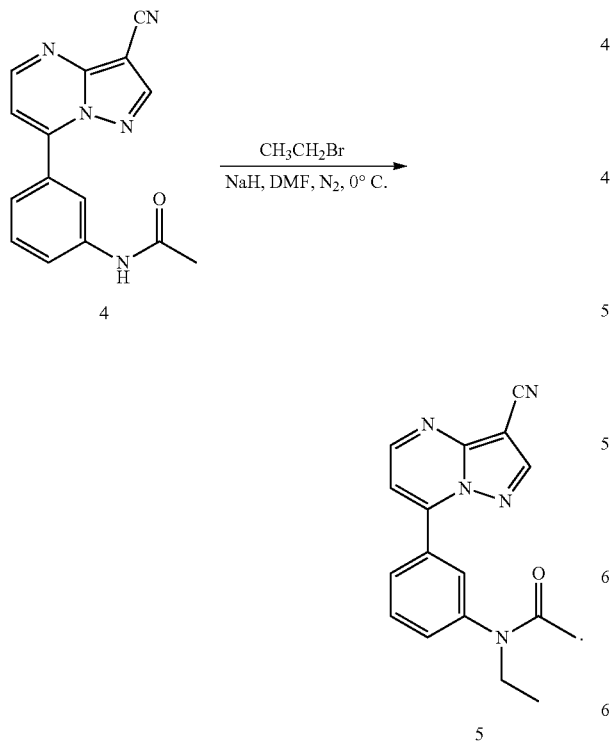

In an embodiment, a molar ratio of the m-nitrobenzaldehyde, the 3-amino-4-cyanopyrazole, the triethylamine, the ammonium iodide and the di-tert-butyl peroxide is 1:1:2:1:3 in that order, and a ratio of the m-nitrobenzaldehyde 1 to the solvent is 1 mmol:4 mL.

Compared with the prior art, the invention has the following advantages and beneficial effects: the preparation method of zaleplon according to the invention adopts simple and cheap m-nitrobenzaldehyde and triethylamine as raw materials, and constructs the core skeleton of zaleplon with high efficiency and high selectivity through a one-pot series reaction without transition metal catalysis, thereby avoiding the formation of isomers, reducing the generation of by-products, increasing the yield of target products and reducing the synthesis cost; after simple nitro reduction modification, zaleplon is prepared. In addition, the method has the advantages of short preparation route, mild reaction conditions and simple operation, so the method is suitable for industrial production.

DETAILED DESCRIPTION OF EMBODIMENTS

The above-mentioned contents of the invention are described in further detail by embodiments below, but it should not be understood that the scope of the above-mentioned subject matter of the invention is limited to the following embodiments, and all technologies based on the above-mentioned contents of the invention belong to the scope of the invention.

Embodiment 1

Preparation of Compound 3

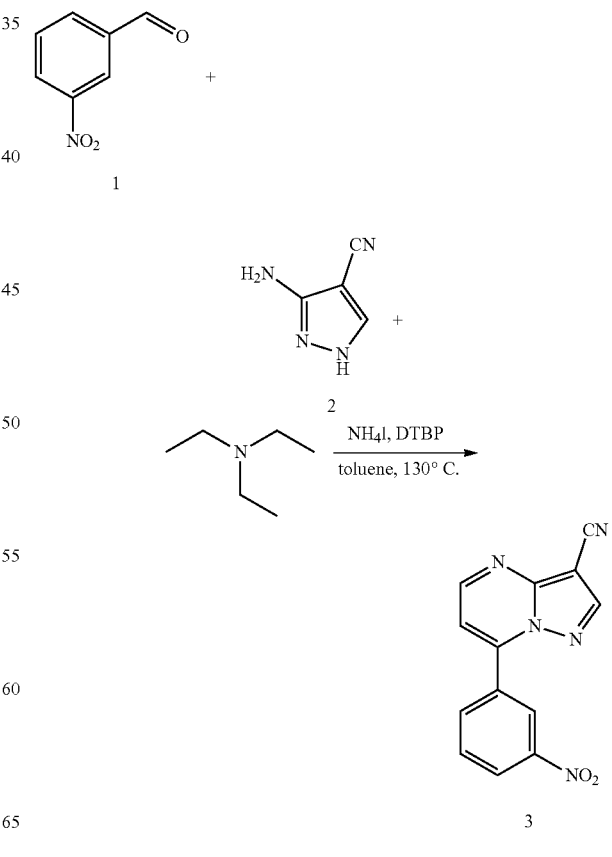

M-nitrobenzaldehyde having the above chemical structural formula 1 (75.5 milligrams (mg), 0.5 millimoles (mmol)), 3-amino-4-cyanopyrazole having the above chemical structural formula 2 (54 mg, 0.5 mmol), triethylamine (101 mg, 1 mmol), ammonium iodide (72.5 mg, 0.5 mmol), di-tert-butyl peroxide (219 mg, 1.5 mmol) and toluene (2 milliliter (mL)) are added into a 35 mL sealed tube, and then the sealed tube is placed in an oil bath at 130° C. and stirred for 10 hours for reaction. 50 mL of water is added to quench the reaction, organic phase is extracted with ethyl acetate (50 mL×3), then the organic phase is washed with $Na_2S_2O_3$ solution with 10% mass concentration and saturated saline solution in turn, and dried with anhydrous sodium sulfate. The organic phase after washed is filtered, spin-dried, and separated by silica gel column (petroleum ether/ethyl acetate=3/1, v/v) to obtain a yellow solid product compound having the above chemical structural formula 3 (also referred to as 7-(3-nitrophenyl) pyrazol[1,5-a]pyrimidine-3-nitrile) (114 mg, 86%). The characterization data of the compound having the above chemical structural formula 3 are as follows: $^1$H NMR (400 MHZ, dimethyl sulfoxide-$d_6$ (DMSO-$d_6$)): δ (ppm) 8.97 (d, J=1.6 Hz, 1H), 8.95 (d, J=4.8 Hz, 1H), 8.88 (s, 1H), 8.48 (dd, J=8.0, 2.0 Hz, 2H), 7.92 (t, J=8.0 Hz, 1H), 7.72 (d, J=4.4 Hz, 1H); $^{13}$C Nuclear Magnetic Resonance (NMR) (100 MHz, DMSO-$d_6$): δ (part per million (ppm)) 153.9, 150.9, 147.5, 147.4, 145.3, 136.2, 130.9, 130.4, 126.2, 124.8, 113.3, 111.3, 81.7; HRMS (ESI) (High Resolution Mass Spectroscopy (Electrospray Spray Ionization)): m/z [M$^+$H]$^+$calcd for $C_{13}H_8N_5O_2$: 266.0673; found: 266.0674.

Embodiment 2

Preparation of Compound 4

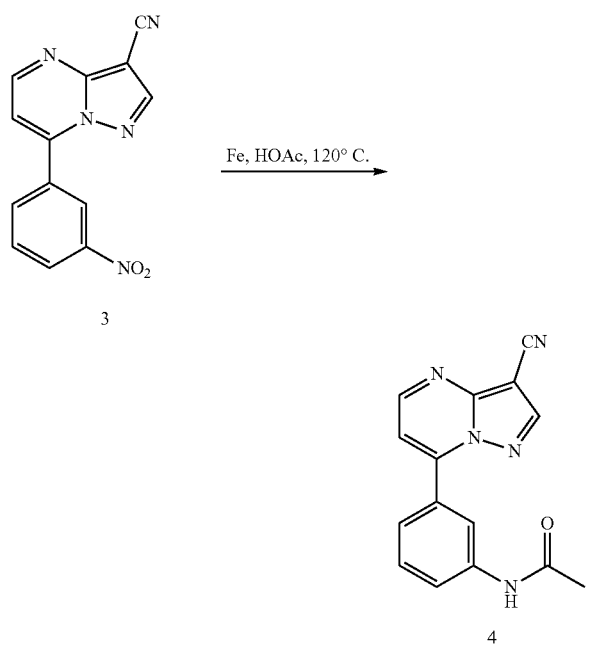

Iron powder (184.8 mg, 3.3 mmol) and glacial acetic acid (20 mL) are added into a three-necked flask, stirred and heated to reflux, acidified for 10 minutes, and the glacial acetic acid (25 mL) solution of compound having the above chemical structural formula 3 (265 mg, 1 mmol) are added dropwise. After addition, continue to reflux for 4 hours. 50 mL water are added to quench the reaction, organic phase is extracted with ethyl acetate (50 mL×3), and then the organic phase is washed with saturated saline solution, and dried the organic phase with anhydrous sodium sulfate. The organic phase after washed is filtered, spin-dried to obtain a white solid compound having the above chemical structural formula 4 (230 mg, 83%). The characterization data of the compound having the above chemical structural formula 4 are as follows: $^1$H NMR (400 MHZ, DMSO-$d_6$): δ (ppm) 10.25 (s, 1H), 8.89 (d, J=4.4 Hz, 1H), 8.86 (s, 1H), 8.32 (t, J=1.8 Hz, 1H), 7.85-7.81 (m, 1H), 7.70-7.67 (m, 1H), 7.54 (t, J=8.0 Hz, 1H), 7.50 (d, J=4.8 Hz, 1H), 2.08 (s, 3H); $^{13}$C NMR (100 MHz, DMSO-$d_6$): δ (ppm) 168.7, 153.8, 151.1, 147.5, 147.3, 139.4, 129.9, 129.1, 124.3, 122.0, 119.9, 113.5, 110.7, 81.4, 24.0; HRMS (ESI): m/z [M$^+$Na]$^+$ calcd for $C_{15}H_{11}N_5NaO$: 300.0856; found: 300.0854.

Embodiment 3

Preparation of Compound 5

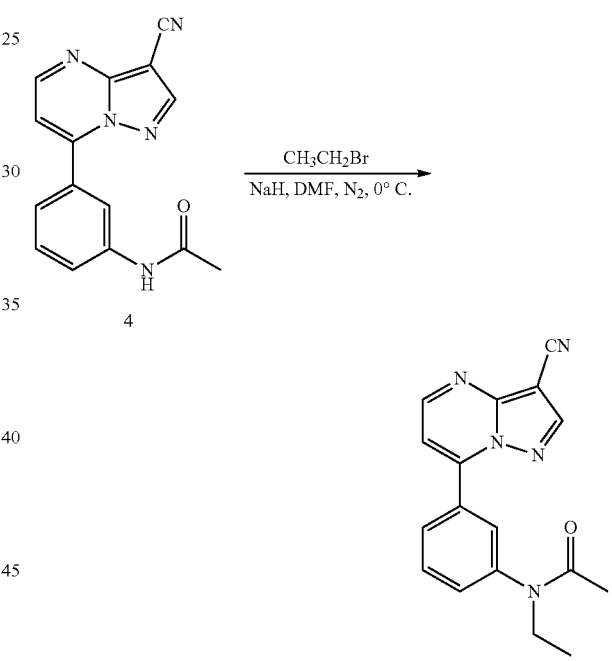

Sodium hydride (58 mg, 2.4 mmol) and anhydrous N,N-dimethylformamide (DMF) (2 mL) are added into a three-necked flask filled with nitrogen, stirred in an ice-water bath, then the DMF (6 mL) solution of compound having the above chemical structural formula 4 (110.8 mg, 0.4 mmol) are added dropwise; reacted for 5 minutes after addition, then bromoethane (436 mg, 4 mmol) are added dropwise, and continued to stir in an ice-water bath for 30 minutes. Organic phase is extracted with ethyl acetate (50 mL×3), and then the organic phase is washed with saturated saline solution and dried the organic phase with anhydrous sodium sulfate. The organic phase after washed is filtered, spin-dried the organic phase to obtain a white solid compound having the above chemical structural formula 5 (103.7 mg, 85%). The characterization data of the compound having the above chemical structural formula 5 are as follows: $^1$H NMR (400

MHZ, DMSO-d$_6$): δ (ppm) 8.92 (d, J=4.4 Hz, 1H), 8.87 (d, J=0.4 Hz, 1H), 8.09 (d, J=7.6 Hz, 1H), 8.04 (s, 1H), 7.71 (t, J=7.8 Hz, 1H), 7.67 (d, J=4.4 Hz, 1H), 7.61 (d, J=7.2 Hz, 1H), 3.70 (q, J=6.8 Hz, 2H), 1.81 (s, 3H), 1.03 (t, J=6.8 Hz, 3H); $^{13}$C NMR (100 MHz, DMSO-d$_6$): δ (ppm) 168.5, 153.8, 151.1, 147.3, 146.6, 142.6, 131.4, 130.7, 129.9, 129.7, 129.0, 113.5, 111.0, 81.4, 43.1, 22.8, 12.9; HRMS (ESI): m/z [M$^+$Na]$^+$calcd for C$_{17}$H$_{15}$N$_5$NaO: 328.1169; found: 328.1171.

The above embodiments have described the basic principles, main features and advantages of the invention. Those skilled in the industry should know that the invention is not limited by the above embodiments. The above embodiments and the description only illustrate the principles of the invention. Any modification, equivalent substitution and change made without departing from the scope of the principles of the invention should be included in the scope of the invention.

What is claimed is:
1. A preparation method of zaleplon, comprising:
S1, preparing 7-(3-nitrophenyl)pyrazol[1,5-a]pyrimidine-3-nitrile having the following chemical structural formula 3, by using m-nitrobenzaldehyde having the following chemical structural formula 1, 3-amino-4-cyanopyrazole having the following chemical structural formula 2 and triethylamine as raw materials in presences of an iodine reagent, an oxidant and a solvent, and a synthetic route therefor being as follows:

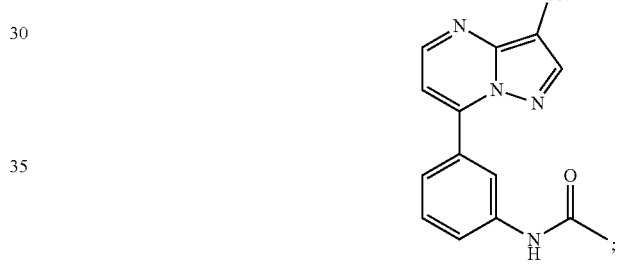

wherein the iodine reagent is one selected from a group consisting of ammonium iodide, N-iodosuccinimide, elemental iodine and tetrabutylammonium iodide; the oxidant is one selected from a group consisting of di-tert-butyl peroxide and dicumyl peroxide; and the solvent is one selected from a group consisting of toluene, chlorobenzene, 1,4-dioxane, acetonitrile and tetrahydrofuran;

S2, subjecting the 7-(3-nitrophenyl)pyrazol[1,5-a]pyrimidine-3-nitrile prepared by the S1 to one-pot reductive acetylation with iron powder and glacial acetic acid to obtain a compound having the following chemical structural formula 4, and a synthetic route therefor being as follows:

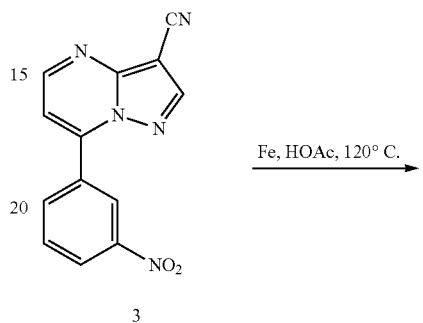

and

S3, ethylating the compound having the chemical structural formula 4 with bromoethane to obtain a compound having the following chemical structural formula 5, wherein the compound having the chemical structural formula 5 is the zaleplon as a target product and a synthetic route therefor is as follows:

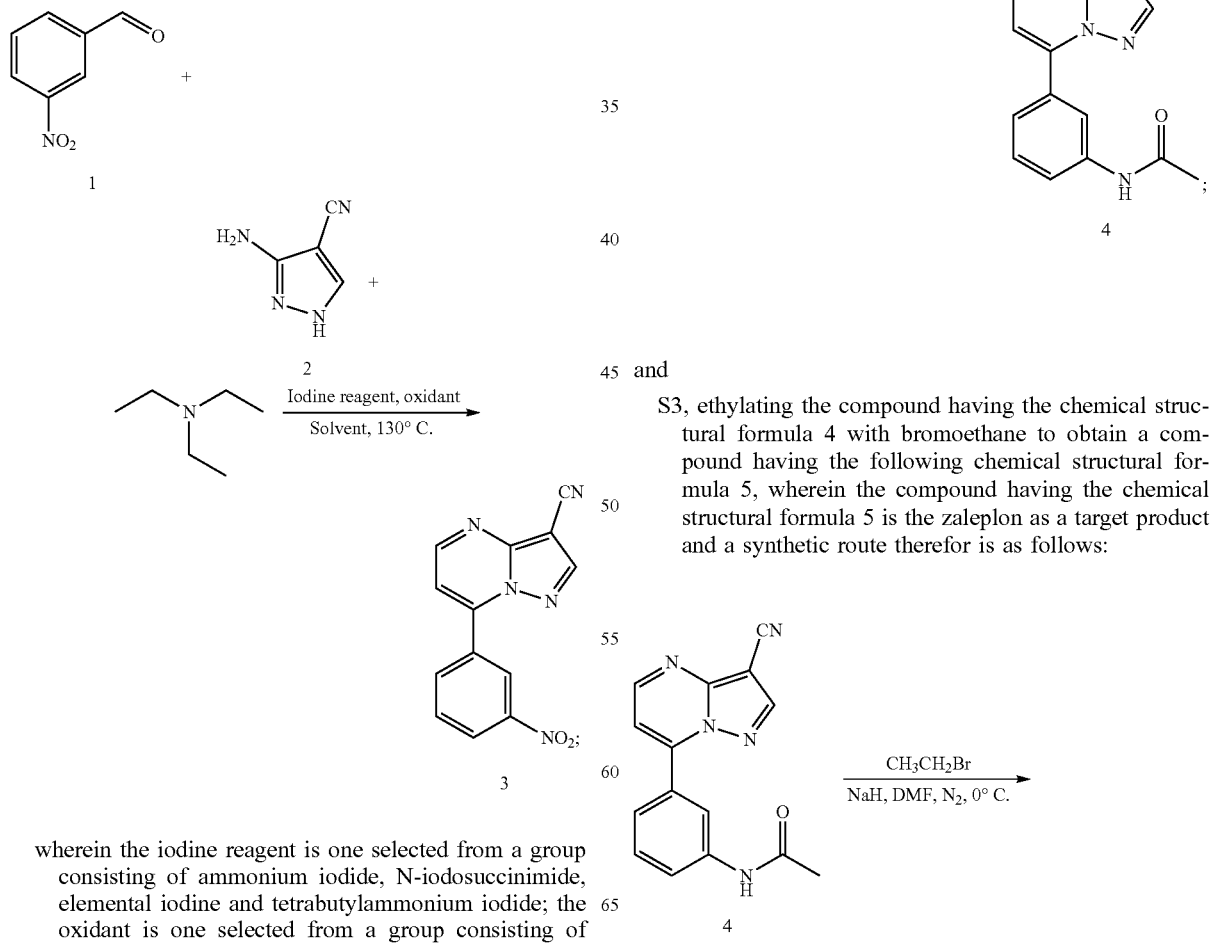

-continued
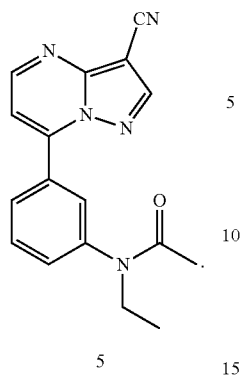
2. The preparation method of zaleplon according to claim 1, wherein a molar ratio of the m-nitrobenzaldehyde, the 3-amino-4-cyanopyrazole, the triethylamine, the ammonium iodide and the di-tert-butyl peroxide is 1:1:2:1:3 in that order, and a ratio of the m-nitrobenzaldehyde to the solvent is 1 millimole (mmol):4 milliliters (mL).
* * * * *